United States Patent [19]
Park et al.

[11] Patent Number: 5,399,737
[45] Date of Patent: Mar. 21, 1995

[54] QUATERNARY AMMONIUM SILOXANE COMPOUNDS AND METHODS FOR THEIR USE

[75] Inventors: Joonsup Park, Arlington, Tex.; Joseph J. Falcetta, Arlington Heights, Ill.

[73] Assignee: Alcon Laboratories, Inc., Fort Worth, Tex.

[21] Appl. No.: 222,790

[22] Filed: Apr. 4, 1994

[51] Int. Cl.⁶ .............................................. C07F 7/10
[52] U.S. Cl. .................................. 556/413; 556/414; 556/418; 556/419; 556/420; 556/424; 556/425
[58] Field of Search ............... 556/413, 424, 425, 418, 556/419, 420

[56] References Cited

U.S. PATENT DOCUMENTS

| | | | |
|---|---|---|---|
| 3,794,736 | 2/1974 | Abbott et al. | 424/78 |
| 4,259,103 | 3/1981 | Malek et al. | 71/67 |
| 4,533,714 | 8/1985 | Sebag et al. | 528/27 |
| 4,587,321 | 5/1986 | Sebag et al. | 528/27 |
| 4,614,675 | 9/1986 | Ona et al. | 427/387 |
| 5,246,607 | 9/1993 | Schaefer et al. | 556/425 X |
| 5,286,890 | 2/1994 | Dougherty | 556/425 |
| 5,300,241 | 4/1994 | Mikami et al. | 556/413 X |

OTHER PUBLICATIONS

Hoover, *J. Macromolo. Sci.–Chem.*, A4 (6) pp. 1327–1417 (Oct. 1970).
Rembaum, *Applied Polymer Symposium*, No. 22, 299–317 (1973).
Petrocci et al., *Dev. Ind. Micro.*, 20, Chapter 1 (1978).
Petrocci, *Disinfection, Sterilization and Preservation*, Third Edition, Chapter 14 (1983).
Hugo et al., *Principle and Practices of Disinfection, Preservation and Sterilization*, Chapter 2 (1982).

Primary Examiner—Paul F. Shaver
Attorney, Agent, or Firm—Sally Yeager

[57] ABSTRACT

Novel quaternary ammonium siloxane compounds and methods for their use are disclosed.

11 Claims, No Drawings

QUATERNARY AMMONIUM SILOXANE COMPOUNDS AND METHODS FOR THEIR USE

BACKGROUND OF THE INVENTION

This invention is directed to novel quaternary ammonium siloxane compounds and their preparation. These compounds are useful as general antimicrobial agents. In particular the compounds are useful in ophthalmic compositions as disinfecting and/or preserving agents. The invention is also directed to methods for using the compounds, particularly in ophthalmic compositions where antimicrobial activity is desired.

The antimicrobial activity of some quaternary ammonium compounds is known; see for example, Petrocci et al., *Dev. Ind. Micro.*, 20, Chapter 1 (1978); Petrocci, *Disinfection, Sterilization and Preservation*, Third Edition, Chapter 14 (1983); Hugo et al., *Principles and Practice of Disinfection, Preservation and Sterilization*, Chapter 2 (1982). In addition, some polymeric quaternary ammonium compounds have also been found to exhibit antimicrobial activity; see Hoover, *J. Macromolo. Sci.-Chem.*, A4 (6) pp. 1327-1417 (October 1970); Rembaum, *Applied Polymer Symposium*, No. 22, 299-317 (1973).

Silanyl and siloxane compounds have been disclosed for their antimicrobial properties in U.S. Pat, No. 4,259,103 issued to Malek et al.; U.S. Pat. No. 4,614,675 issued to Ona et al. and U.S. Pat. No. 3,794,736 issued to Abbott et al.

U.S. Pat. Nos. 4,587,321 and 4,533,71 4, both issued to Sebag et al. disclose quaternary ammonium siloxane polymers. These patents do not disclose the compounds of the present invention which are siloxane quaternary ammonium compounds, some of which are polymeric siloxane quaternary ammonium compounds.

SUMMARY OF THE INVENTION

This invention is directed to new siloxane quaternary ammonium compounds and their preparation. The compounds are useful as antimicrobial agents. In particular the compounds are useful as disinfecting and/or preserving agents in ophthalmic formulations. Ophthalmic formulations can include contact lens disinfecting solutions, preserved contact lens solutions and preserved pharmaceutical formulations.

The invention is also directed to methods for using the compounds. In particular, formulations of the compounds can be used to disinfect contact lenses, and preserve contact lens care solutions and ophthalmic formulations.

DETAILED DESCRIPTION OF PREFERRED EMBODIMENTS

The compounds of this invention are quaternary ammonium siloxanes of the following general formulas I-V:

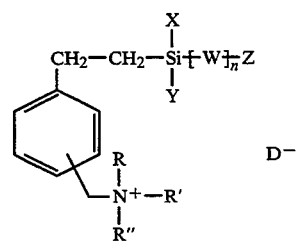

wherein:

X and Y are $C_1$-$C_5$ alkyl, phenyl, or W, wherein W has the structure:

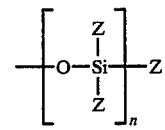

Z is $C_1$-$C_5$ alkyl or phenyl and n is an integer from zero to five.

R, R', R" are the same or different and are $C_1$-$C_{20}$ alkyl, benzyl or substituted benzyl, aromatic or substituted aromatic, cycloalkyl or substituted cycloalkyl; and $D^-$ is an anion, preferably a pharmaceutically acceptable anion.

Preferred compounds within structure [I] have the following general structure with A and R defined in Table 1.

TABLE 1

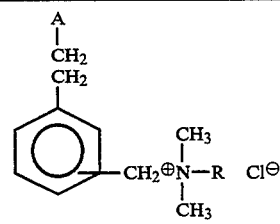

| Compound | A | R |
|---|---|---|
| IA | —Si[OSi(CH$_3$)$_3$]$_3$ | —CH$_3$ |
| IB | —Si[OSi(CH$_3$)$_3$]$_3$ | —CH$_2$—Ar |
| IC | —Si[OSi(CH$_3$)$_2$OSi(CH$_3$)$_3$]$_3$ | —CH$_3$ |
| ID | —Si[OSi(CH$_3$)$_2$OSi(CH$_3$)$_3$]$_3$ | —CH$_2$—Ar |
| IE | —Si(CH$_3$)$_2$OSi(CH$_3$)$_3$ | —CH$_2$—Ar |
| IF | —Si(CH$_3$)$_2$OSi(CH$_3$)$_3$ | —CH$_3$ |
| IG | —SiCH$_3$[OSi(CH$_3$)$_3$]$_2$ | —CH$_2$—Ar |

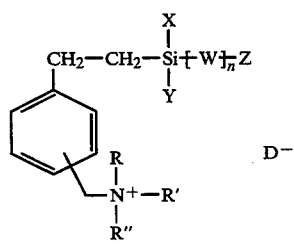

wherein:

X and Y are $C_1$-$C_5$ alkyl, phenyl, or W, wherein W has the structure:

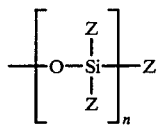

and Z is $C_1$–$C_5$ alkyl or phenyl and n is an integer from zero to five.

R, R', R" are the same or different radicals and are $C_1$–$C_{20}$ alkyl, benzyl or substituted benzyl, aromatic or substituted aromatic, cycloalkyl or substituted cycloalkyl; or R, R', and R" are the same or different and are $C_1$–$C_{20}$ aliphatic hydrophilic radicals; and D⁻ is an anion, preferably a pharmaceutically acceptable anion.

Preferred compounds within structure [II] have the following general structure and A, R, and R' are defined in Table 2.

TABLE 2

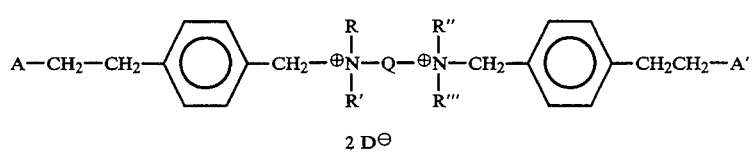

| Compound | A | R | R' |
|---|---|---|---|
| IIA | —Si[OSi(CH₃)₃]₃ | —CH₃ | —CH₂CH₂OH |
| IIB | —Si[OSi(CH₃)₃]₃ | —CH₃ | —CH₂CH₂CH₂OH |
| IIC | —Si[OSi(CH₃)₃]₃ | —CH₂CH₂OH | —CH₂CH₂OH |
| IID | —Si[OSi(CH₃)₃]₃ | —CH₃ | —CH₂CH₂N(H)—C(=O)—N(H)CH₂CH₃ |
| IIE | —SiCH₃[OSi(CH₃)₃]₂ | —CH₃ | —CH₂CH₂CH₂OH |
| IIF | —SiCH₃[OSi(CH₃)₃]₂ | —CH₃ | —CH₂CH₂OH |

$$A-CH_2-CH_2-\phi-CH_2-\overset{R}{\underset{R'}{\overset{\oplus}{N}}}-Q-\overset{R''}{\underset{R'''}{\overset{\oplus}{N}}}-CH_2-\phi-CH_2CH_2-A' \quad [III]$$

2 D⁻ wherein:

A and A' are the same or different and have the structure:

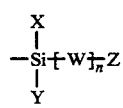

wherein:

X and Y are $C_1$–$C_5$ alkyl, phenyl, or W; wherein W has the structure:

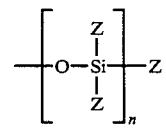

and Z is $C_1$–$C_5$ alkyl or phenyl and n is an integer from zero to five.

R, R', R", R''' are the same or different and am $C_1$–$C_{20}$ alkyl, benzyl or substituted benzyl, aromatic or substituted aromatic, or cycloalkyl or substituted cycloalkyl.

Q is a radical of linear or branched $C_2$–$C_{20}$ alkyl, unsaturated $C_3$–$C_{20}$ alkyl; $C_2$–$C_{20}$ alkyloxy, aryl or alkyl aryl substituted or unsubstituted, cycloalkyl or substituted cycloalkyl, or a heteroalkyl structure in which the quaternary ammonium atom may or may not be part of the heteroalkyl structure; and D⁻ is an anion, preferably a pharmaceutically acceptable anion.

Preferred compounds within Structure [III] have the following general structure and A and X are defined in Table 3.

TABLE 3

$$A-CH_2CH_2-\phi-CH_2-\overset{CH_3}{\underset{CH_3}{\overset{\oplus}{N}}}-X-\overset{CH_3}{\underset{CH_3}{\overset{\oplus}{N}}}-CH_2-\phi-CH_2CH_2A$$

| Compound | A | —X— |
|---|---|---|
| IIIA | —Si[OSi(CH₃)₃]₃ | —CH₂CH₂CH₂CH₂— |
| IIIB | —Si[OSi(CH₃)₃]₃ | —CH₂CH₂CH₂CH₂CH₂CH₂— |
| IIIC | —Si[OSi(CH₃)₃]₃ | —CH₂CH₂— |
| IIID | —Si[OSi(CH₃)₃]₃ | —CH₂CH=CH—CH₂— |

TABLE 3-continued

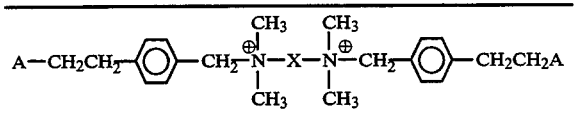

Com-

| pound | A | —X— |
|---|---|---|
| IIIE | —Si(CH$_3$)$_2$OSi(CH$_3$)$_3$ | —CH$_2$CH$_2$CH$_2$CH$_2$— |
| IIIF | —Si(CH$_3$)$_2$OSi(CH$_3$)$_3$ | —CH$_2$CH$_2$— |

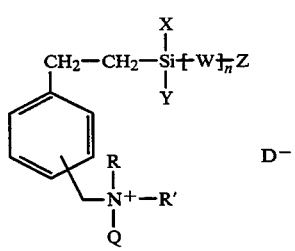
[IV]

wherein:

X and Y are C$_1$-C$_5$ alkyl, phenyl, or W, wherein W has the structure:

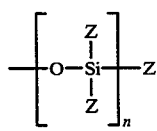

and Z is C$_1$-C$_5$ alkyl or phenyl and n is an integer from zero to five.

R, R' are the same or different and are C$_1$-C$_{20}$ alkyl, benzyl or substituted benzyl, aromatic or substituted aromatic, cycloalkyl;

Q is alkyl, aryl, or cycloalkyl having a polymerizable vinyl group; and

D$^-$ is an anion, preferably a pharmaceutically acceptable anion.

Preferred compounds within Structure [IV] have the following general formula and A and R are defined in Table 4.

TABLE 4

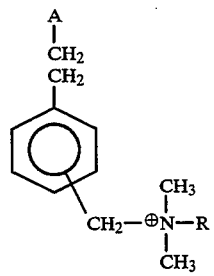

| Compound | A | R |
|---|---|---|
| IVA | —Si[OSi(CH$_3$)$_3$]$_3$ | —CH$_2$CH$_2$O—C(=O)—C(CH$_3$)=CH$_2$ |
| IVB | —Si[OSi(CH$_3$)$_3$]$_3$ | —CH$_2$CH$_2$CH$_2$—N(H)—C(=O)—C(CH$_3$)=CH$_2$ |
| IVC | —Si(CH$_3$)$_2$OSi(CH$_3$)$_3$ | —CH$_2$CH$_2$O—C(=O)—C(CH$_3$)=CH$_2$ |
| IVD | —Si(CH$_3$)$_2$OSi(CH$_3$)$_3$ | —CH$_2$CH$_2$CH$_2$—N(H)—C(=O)—C(CH$_3$)=CH$_2$ |

In addition to the quaternary ammonium siloxane compounds depicted in structures [I] through [IV], this invention comprises a fifth group of quaternary ammonium siloxane compounds which are homopolymers and copolymers prepared from the monomers of structure [IV]. These homopolymers and copolymers are prepared by the applicable method of addition polymerization. The resulting compounds are microbiologically active and are advantageously used when it is beneficial to have a compound which has a hydrophobic group in addition to exhibiting antimicrobial activity. For example, it can be desirable to use such a compound in contact lens care solutions and preparations which will be used with hydrophilic soft contact lenses.

Polymeric compounds of the present invention are represented by the following structures:

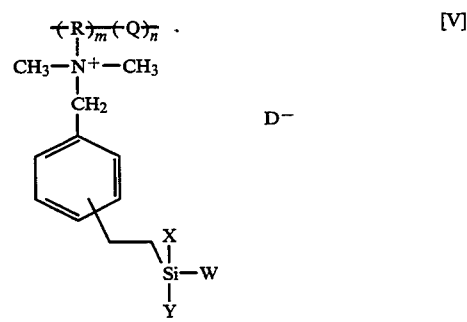
[V]

wherein:

R is alkyl, aryl, or cyloalkyl having a polymerizable vinyl group; X and Y are $C_1$-$C_5$ alkyl, phenyl, or W wherein W has the structure:

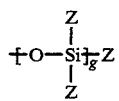

and Z is a $C_1$-$C_5$ alkyl or phenyl and g is an integer from zero to five.

Q is an alkyl, aryl or cycloalkyl having a polymerizable and a water compatible functional group; and D⁻ is a pharmaceutically acceptable anion,
The letters m and n are the ratio of two monomers.

Preferred compounds within Group V can be represented by the following structure with m and n defined in Table 5.

TABLE 5

| Compound | m | n |
|----------|---|---|
| VA | 1 | 0 |
| VB | 1 | 1 |
| VC | 1 | 2 |
| VD | 1 | 3 |
|    | 2 | 1 |

The compounds of the present invention can be used in compositions or formulations in which antimicrobial activity is desired. Depending on the intended antimicrobial use, the compounds can be present at concentrations up to and including about 1%. When the compounds are used as disinfectants or preservatives in ophthalmic compositions the compounds can be present at concentrations between about 0.00001 and 0.1 wt. %, preferably 0.001 to 0.01 wt. %.

The preferred antimicrobial compounds are those represented by structures [II] and [V]. The compound defined by [II] which is most preferred is [IIC]. Compounds defined by [II] exhibit antimicrobial activity similar to that of BAC but are relatively less toxic. This makes the compounds more desirable for use in areas where reducing toxicity and the associated discomfort are very important, such as for use in the eye. The compound within [V] which is most preferred is [VB]. Compounds defined by [IV] exhibit antimicrobial activity and are particularly useful in conjunction with soft contact lenses, such as high water content soft contact lenses.

EXAMPLE 1

Synthesis of tris(trimethylsiloxy)silylethyl-m,p-benzyl trimethyl ammonium chloride [IA]

A. Synthesis of tris(trimethylsiloxy)silane-m,p-chloromethyl phenylethane

A catalyst solution is prepared by adding, with stirring, 23.8 g of concentrated sulfuric acid to a solution of 11.6 g of ethanol in 16.5 ml of distilled water. To a 500 ml round bottom flask that is situated on an ice bath, a mixture of 43.6 g (0.33 mole) of trimethylacetoxysilane and 27.4 g (0.1 mole) of trimethoxysilane-m,p-chloromethyl phenylethane is added. To this mixture 9.1 ml of the catalyst solution is added in a dropwise manner over a time period of 30 minutes. The reaction mixture is vigorously stirred for three days at room temperature. After separation, the organic layer is neutralized with sodium bicarbonate, washed with water and dried over magnesium sulfate. A yield of 31 g (69.2%) of a slightly yellow liquid having an index of refraction of 1.4515 is obtained at 120°-135° C. (0.3-0.4 mmHg). The identity of the compound was confirmed by the infrared spectrum and nmr spectrum [7.1 ppm (m,4H), 0.0 ppm (s,27H)].

B. Synthesis of tris(trimethylsiloxy)silylethyl-m,p-benzyl trimethyl ammonium chloride [IA]

The chloromethyl compound prepared in A (4.48 g, 0.01 mole) and a ten fold excess of a 25% aqueous solution of trimethylamine were dissolved in 50 ml of isopropanol and treated for three hours in an pressure bottle at 85° C. The resulting mixture was evaporated in vacuo to a glassy material that was dissolved in ethyl ether, extracted twice with water, dried over anhydrous magnesium sulfate and evaporated in vacuo. The resulting material was purified by column chromatography using a silica gel column and ethyl acetate-ethanol (50:50) as the solvent. A 60% yield of Compound [IA] was obtained. The identity of the compound was confirmed by nmr: 7.3 ppm (b,4,aromatic), 4.8 ppm (s,2,N—CH₂), 3.3 ppm (s,9,N—CH₃) and 0.0 ppm (s,27,SiCH₃). Further structural confirmations were obtained by elemental analysis and analysis of the infrared spectrum. The structure of each compound was confirmed by nmr. [IB], [IC], [ID], [IE] and [IF] were synthesized in a manner similar to [IA]. The structures of each were confirmed by nmr as shown in Table 1. Further structural confirmation was obtained by elemental analysis and infrared spectrum.

TABLE 5

Compounds IB through IF

| Compound | nmr |
|----------|-----|
| IB tris(trimethylsiloxy)silylethyl-m-p-benzyl dimethyl benzyl ammonium chloride | 7.7-7.0 ppm(b, 9, aromatic), 5.1 and 4.8 ppm(2s, 4, N—CH₂), 3.0 ppm(s, 6, N—CH₃) and 0.0 ppm(s, 27, Si—CH₃) |
| IC tris(pentamethyldisiloxy)silylethyl-m,p-benzyl trimethyl ammonium chloride | 7.5-7.1 ppm(b, 4, aromatic), 4.8 ppm(s, 2, CH₂—N), 3.9 ppm(s, 9, N—CH₃), 0.0 ppm(m, 45, Si—CH₃) |
| ID tris(pentamethyldisiloxy)silylethyl-m,p-benzyl dimethyl benzyl | 7.7-7.0 ppm(b, 9 aromatic), 5.1 and 4.8 ppm(2s, 4, N—CH₂), |

TABLE 5-continued

Compounds IB through IF

| Compound | nmr |
|---|---|
| ammonium chloride | 3.0 ppm(s, 6, N—CH$_3$) and 0.0 ppm(s, 27, Si—CH$_3$) |
| IE trimethylsiloxydimethylsilylethyl-m,p-benzyl dimethyl benzyl ammonium chloride | 7.6–6.6 ppm(b, 9, aromatic), 5.3 and 4.8 ppm(b, 4, CH$_2$—N—CH$_2$), 3.1 ppm(s, 6, N—CH$_3$), 0.0 ppm(m, 15, Si—CH$_3$) |
| IF trimethylsiloxydimethylsilylethyl-m,p-benzyl trimethyl ammonium chloride | 7.6–6.9 ppm(b, 4, aromatic), 4.8 ppm(s, 2, N—CH$_2$), 3.4 ppm(s, 9, N—CH$_3$), 0.0 ppm(s, 15, Si—CH$_3$) |

EXAMPLE 2

Synthesis of bis(trimethylsiloxy)methylsilylethyl benzyl dimethyl benzyl ammonium chloride [IG]

A mixture of 3.74 bis(trimethylsiloxy) methylsilylethyl benzyl chloride and 1.38 g of N,N-dimethylbenzylamine in isopropanol was treated at 80° C. for 4 hours and then evaporated in vacuo. The resulting glassy material was treated 5 times with n-hexane and then crystallized from ethyl acetate-n-hexane. A yield of 0.8 g (16%) of Compound [IG] was obtained. The structure of the compound was confirmed by elemental analysis, infrared spectroscopy, mass spectroscopy and nmr. The nmr data showed: 7.7–7.0 ppm (b,4 aromatic), 5.1 ppm (b,4,N—CH$_2$), 3.1 ppm (s,6,N—CH$_3$) and 0.0 ppm (s, 21 ,Si—CH$_3$).

EXAMPLE 3

Synthesis of Benzenemethanaminium, N,N-dimethyl,N-3-hydroxypropyl-3,4-{2-[bis(trimethylsiloxy)methyl silyl]ethyl}-,chloride [IIE]

N,N-dimethylpropan-1-ol (1.03 g) and 3.74 g (0.01 mole) bis(trimethylsiloxy)methyl silylethyl benzyl chloride were added to 100 ml of isopropanol and heated at 83° C. for five hours. The resulting reaction mixture was concentrated in vacuo. A crystalline product (3.2 g) was obtained by dissolving the product in isopropanol and precipitation from n-hexane. This procedure was repeated three times. The structure of the compound was confirmed by elemental analysis and spectroscopic analysis including nmr: 7.9–7.0 ppm (b, 4,aromatic), 5.2 [b,1,—OH (exchangeable with D$_2$O)], 4.8 ppm (s,2,O—CH$_2$—N), 3.6 ppm (b,4,N CH$_2$CH$_2$CH$_2$OH) 3.1 ppm (s,6,N—CH$_3$), 2.1 ppm (b,2, N CH$_2$ CH$_2$CH$_2$OH) and 0.0 ppm (2s, 21, Si—CH$_3$)

Compounds [IIA], [IIB] and [IIF] were prepared in a manner similar to Compound [IIE]. Structures were confirmed by elemental analysis and spectroscopy. The nmr data for each compound is shown in Table 6.

TABLE 6

Compounds IIA, IIB, IIF

| Compound | nmr |
|---|---|
| IIF benzenemethanaminium,N,N-dimethyl,N-2-hydroxyethyl-3,4-{2-[bis(trimethylsiloxy)methyl silyl]ethyl}-,chloride | 7.5 ppm(b, 4, aromatic), 5.7 ppm(b, 1, OH) 4.7 ppm(s, 2, —CH$_2$—N), 4.1 and 3.6 ppm(2s, 4, CH$_2$—CH$_2$—OH), 3.2 ppm(s, 6, N—CH$_3$) and 0.0 pm(2s, 21, Si—CH$_3$) |
| IIA benzenemethanaminium,N,N-dimethyl,N-2-hydroxyethyl-3,4-{2-[tris(trimethylsiloxy)silyl]ethyl}-, chloride | 7.3–6.9 ppm(b, 4, aromatic), 5.7 ppm(b, 1, OH) 4.7 ppm(s, 2, —CH$_2$—N), 4.1 and 3.6 ppm(2s, 4, CH$_2$—CH$_2$—OH), 2.8 ppm(s, 6, N—CH$_3$) and 0.0 ppm(2s, 27, Si—CH$_3$) |
| IIB benzenemethanaminium,N,N-dimethyl,N-3-hydroxypropyl-3,4-{2-[tris(trimethylsiloxy)silyl]ethyl}-, chloride | 7.5–7.0 ppm(b, 4, aromatic), 5.1 ppm(s, 1, OH), 4.7 ppm(s, 2, O—CH$_2$—N), 3.2 ppm(s, 6, N—CH$_3$), 0.0 ppm(s, 27, Si—CH$_3$) |

EXAMPLE 4

Synthesis of benzenemethanaminium,N,N-dimethyl,N-2-(3-ethylureido)ethyl-3,4-{2-[tris(trimethylsiloxy)silyl]ethyl}-,chloride [IID]

A flask containing 3.55 g (0.05 mole) of ethylisocyanate dissolved in 20 ml methylene chloride was placed in an ice bath. A solution of 4.4 g (0.05 mol) N,N-dimethylethylene diamine in 10 ml methylene chloride was added in a dropwise manner. The reaction mixture was allowed to reach room temperature, stirred for 2 hours and then concentrated in vacuo. The resulting liquid was treated 3 times with n-hexane to yield 6.0 g (86%) 1-N-ethyl-N-(N,N-dimethylaminoethyl)urea.

Tris(trimethylsiloxy)silylethenylbenzyl chloride (4.48 g, 0.01 mole) in 60 ml isopropanol was refluxed for 3 hours with 1.59 g (0.01 mole) 1-N-ethyl-N-(N,N-dimethylaminoethyl)urea. A glassy material was obtained after concentration of the reaction mixture. This material was purified by dissolving in a 75:25 mixture of acetonitrile-water and application to a reverse phase column. Compound [IID] was obtained in a 64% yield (3.9 g). The structure of the compound was confirmed by elemental analysis and by spectroscopic analysis including nmr: 7.4–6.9 ppm (b,4,aromatic), 6.1 ppm (b,2,N—H), 4.7 ppm (S.2,—CH$_2$—N), 3.7 ppm (M,4,NHCH$_2$), 3.1 ppm (b,8,N—CH$_3$ and N—CH$_2$), 1.0 ppm (t,3,CH$_2$CH$_3$) and 0.0 ppm (s,27,Si—CH$_3$).

EXAMPLE 5

Synthesis of benzenemethanaminium,N-methyl,N,N-2-dihydrox-yethyl-3,4-{2-[tris(trimethylsiloxy)silyl]ethyl}-,chloride (IIC)

A mixture of tris(trimethylsiloxy)silylethenylbenzyl chloride (7.9 g, 0.01 7 mol) and 2.5 g (0.021 mol) N-methyl diethanol amine in 120 ml isopropanol was refluxed for 16 hours. The reaction mixture was concentrated in vacuo. The resulting oily material was dissolved in 130 ml ethyl acetate. The ethyl acetate solution was washed with saturated NaCl solution (3 times with 20 ml each time) and dried over anhydrous sodium sulfate. A syrup like material was obtained after evaporation of the ethyl acetate. This material was treated 3 times with 50 ml n-hexane to yield a light yellow paste. After drying the desired product was obtained in 60% yield.

The structure of the compound was confirmed by elemental analysis and spectroscopic analysis including nmr: 7.5–7.0 ppm (b,4,aromatic), 5.5 ppm (b, 2,OH), 4.8 ppm (s,2,N—CH$_2$—O), 3.2 ppm (s,3,N—CH$_3$), 0.0 ppm (s,27,Si—CH$_3$).

EXAMPLE 6

Synthesis of 1,4-butanediaminium,N,N,N',N'-tetramethyl-N,N'-di-3,4-{2-[-tris(trimethyl siloxy)silyl]ethyl}benzyl-,dichloride [IIIA]

Isopropanol (40 ml) was added to a round bottom flask along with 3.34 g (0.0074 mole) tris(trimethylsiloxy)silylethenyl benzyl chloride and 0.48 g (0.0033 mole) N,N,N',N'-tetramethyl-1,4-butanediamine. The mixture was refluxed at 95° C. for 3 hours. After removal of the solvent the residue was treated 3 times with n-hexane to yield 1.14 g (33% yield) of a white solid.

The structure of the compound was confirmed by elemental analysis and spectroscopic analysis including nmr: 7.2 ppm (b,8,aromatic), 4.6 ppm (b,4,0CH$_2$—N), 3.1 ppm (s,12,N—CH$_3$), 0.0 ppm (s,54, Si—CH$_3$).

Compounds [IIIB]-[IIIF] were prepared in a manner similar to Compound [IIIA]. Structures were confirmed by elemental analysis and spectroscopy. The nmr data for each compound is shown in Table 7.

TABLE 7

| Compound | | nmr |
|---|---|---|
| IIIB | 1,6-hexanediaminium,N,N,N',N'-tetramethyl-N,N'-di-3,4-(2-[tris(trimethyl siloxy)silyl]ethyl)benzyl-,dichloride | 7.5–7.0(b, 8, aromatic), 4.8(s, 4, N—CH$_2$O), 4.0–3.5(b, 4, N—CH$_2$CH$_2$), 3.3(S, 12, N—CH$_3$), 2.3–1.8(b, 8, CH$_2$), 0.09(s, 54, Si—CH$_3$) |
| IIIE | 1,4-butanediaminium,N,N,N',N'-tetramethyl-N,N'-di-3,4-[2-(trimethylsiloxy dimethyl silyl)ethyl]benzyl-,dichloride | 7.5–7.0(13.8, aromatic), 4.8(s, 4, N—CH$_2$O—): 4.0–3.9(b, 4, N(CH$_2$CH$_2$). 3.3(s, 12, N—CH$_3$) 2.5(b, 4, CH$_2$), 0.0(s, 54, Si—CH$_3$) |
| IIID | 1,2-ethanediaminium,N,N,N',N'-tetramethyl-N,N'-di-3,4-(2-[tris(trimethylsiloxy)silyl]ethyl)benzyl-,dichloride | 7.5–7.0 ppm(b, 1, aromatic), 4.8 ppm(S, 4, N—CH$_2$—O), 3.2 ppm(s, 12, N—CH$_3$), 0 ppm(s, 54, Si—CH$_3$) |
| IIIC | 1,4-but-2-enediaminium,N,N,N',N'-tetramethyl-N,N'-di-3,4-(2-[tris(trimethylsiloxy)silyl]ethyl)benzyl-,dichloride | 7.5–7.0 ppm(b, 10, aromatic and CH=CH), 4.8 ppm(s, 4, N—CH$_2$—O), 4.4(B, 4, N—CH$_2$—CH=), 3,2 ppm(s, 12, N—CH$_3$), 0.0 ppm(s, 54, Si—CH$_3$) |
| IIIF | 1,2-ethanediaminium,N,N,N',N'-tetramethyl-N,N'-di-3,4-[2-(trimethylsiloxy dimethyl silyl)ethyl]benzyl-,dichloride | 7.5–7.0 ppm(b, 8, aromatic), 4.8 ppm(s, 4, N—CH$_2$—O), 3.6 ppm(s, 4, N—CH$_2$CH$_2$), 3.1 ppm(s, 12, N—CH$_3$), 0.0 ppm(s, 54, Si—CH$_3$) |

EXAMPLE 7

Synthesis of benzenemethanaminium,N,N-dimethyl,N-methacryloxyethyl-3,4-{2-[tris(trimethylsiloxyl)silyl]ethyl},-chloride IVA N,N-dimethylaminoethyl methacrylate (1.57 g, 0.01 mole) and 4.48 g (0.01 mole) tris(trimethylsiloxy)silylethenyl benzyl chloride were refluxed in isopropanol for 4 hours in the presence of a small amount of the inhibitor, 2.5-diphenyl-p-benzoquinone (DPQ). The glassy material that was obtained after the removal of the solvent was treated twice with n-hexane to yield 5.2 g (87%) of the desired product.

The structure of the compound was confirmed by elemental analysis and spectroscopic analysis including nmr: 7.4–6.9 ppm (m,4,aromatic), 5.9 and 5.4 ppm (2s, 2, CH$_2$=), 4.9 ppm (s, 2, N—CH$_2$—O), 4.5 and 4.0 ppm (2s, 4, N—CH$_2$CH$_2$O), 3.2 ppm (s,6,N—CH$_3$), 1.8 ppm (s,3,CH$_2$=C—CH$_3$) and 0.0 ppm (s, 27,Si—CH$_3$).

EXAMPLE 8

Synthesis of benzenemethaminium, N,N-dimethyl,N-methacrylamidopropyl-3,4-{2-[tris(-trimethylsiloxyl)silyl]ethyl},-chloride IVB Following the same general procedure as in Examples 1–9, a mixture of 4.48 g (0.01 mole) tris(trimethylsiloxy)silylethenyl benzyl chloride and 1.7 g (0.01 mole) N,N-dimethylpropyl methacrylamide was refluxed for 5 hours in 50 ml isopropanol. After solvent removal and treatment with n-hexane 5.0 g (81% yield) of purified product were obtained.

The nmr data for the compound was: 8.1 ppm (b,1 ,N—H), 7.3–6.9 ppm (b,4,aromatic), 5.8 and 5.1 ppm (2s, 2,CH$_2$—), 4.0 to 3.2 ppm (b,4,NCH$_2$CH$_2$CH$_2$N), 2.1 ppm (b,2,NCH2CH2CH2N), 1.9 ppm (s,3,CH2=C—CH3) and 0.0 ppm (s,27,Si—CH3).

EXAMPLE 9

Synthesis of benzenemethanaminium,N,N-dimethyl,N-methacryloxyethyl-3,4-(2-trimethylsiloxydimethylsilyl)ethyl],-chloride [IVC]

Following the same general procedure as in Examples 1-8, 4.0 g (0.01 3 mole) tris(pentamethyldisiloxy)-silylethenyl benzyl chloride was reacted with 2.3 g (0.015 mole) N,N-dimethylaminoethyl methacrylate to yield 3.5 g (57%) of the desired purified product.

The nmr data for the compound was: 7.2 ppm (b,4,aromatic), 5.9 and 5.4 ppm (2s,2,C=CH2), 4.9 ppm (s,2,0—CH2—N), 3.2 ppm (s,6,NCH3), 1.8 ppm (s,3,CH2—C—CH3), 0.0 ppm (m, 15,Si—CH3).

EXAMPLE 10

Synthesis of benzenemethanaminium,N,N-dimethyl,N-mathacrylamidopropyl-3,4-[2-(trimethylsiloxydimethyl silyl)ethyl],-chloride [IVD]

Following the same general procedure as in Example 1-9, 4.47 g (0.015 mole) tris(pentamethylsiloxy)-silylethenyl benzyl chloride was reacted with 3.03 g (0.018 mole) N,N-dimethylpropyl methacrylamide to yield 5.68 g (81%) of the desired purified product.

The nmr data for this compound was: 8.1 ppm (b,1 ,CO—N—H), 7.1 ppm (b,4,aromatic), 5.9 and 5.2 ppm (2s,2,CH3—C=CH2), 4.6 ppm (s,2,0 CH2N), 3.1 ppm (s,6,NCH3), 1.9 ppm (s,3,CH2=C—CH3), 0.0 ppm (m,15,Si—CH3).

EXAMPLE 11

Homopolymer of benzenemethanaminium,N,N-dimethyl,N-methacryloxyethyl]-ethyl-3,4-{2-[tris(trimethylsiloxyl)silyl]ethyl},-chloride [VA]

Dioxane was used as a solvent for all polymerizations, before use it was freshly distilled from LiAlH4. Benzene-methanaminium,N,N-dimethyl,N-methacryloxyethyl-3,4-{2-[tris(trimethylsiloxyl)silyl]ethyl},-chloride, 1.0 g was added to a clean, dry 20 ml glass, screw top test tube along with 10 ml dioxane, 10mg of azobisisobutylonitrile. After degassing with Argon the tube was capped and placed in an oil bath at 60° C. for one hour and then the temperature was raised to 70° C. and the polymerization was allowed to proceed overnight. A white precipitate was formed that was dissolved in methanol and precipitated from ethyl ether. A 70% yield of polymer was obtained. The homopolymer was essentially insoluble in water but was soluble in methanol, dimethyl formamide and other polar organic solvents.

The structure was confirmed by the following peaks in IR: 3400 CM-1, 1730 (ester), and 1060 (Si—O).

EXAMPLE 12

Copolymers of benzenemethanaminium, N,N-dimethyl, N-methacryl oxyethyl-3,4-{2-[tris(trimethylsiloxy)silyl]ethyl},-chloride and acrylamide (1:1 copolymer) [VB]

Using the same procedure as Example II, copolymers were prepared of acrylamide (0.1 g, $1.43 \times 10^{-3}$ moles) and 0.850 g ($1.40 \times 10^{-3}$ moles) of benzenemethaniminium, N,N-dimethyl, N-methacryloxyethyl-3,4{2-[tris(trimethylsiloxysilyl]ethyl},-chloride. A1BN was used to initiate the polymerization. The reaction yielded 45% of the product. The polymer was characterized by determining the intensity of peaks at 1730 cm$^{-1}$ and 1680 cm$^{-1}$.

The same procedure is utilized to synthesize copolymers of the followings: 2:1 and 3:1 ratios of siloxanyl compound and acrylamide.

We claim:

1. Compounds of the structure:

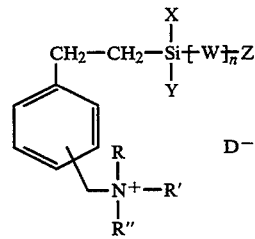

wherein:

and Y are C$_1$–C$_5$ alkyl, phenyl, or W groups, wherein W has the structure:

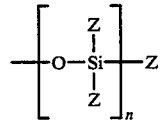

and Z is C$_1$–C$_5$ alkyl or phenyl and n is an integer from zero to five; and

R, R', R" are the same or different and are C$_1$–C$_{20}$ alkyl, benzyl or substituted benzyl, aromatic and substituted aromatic, cycloalkyl or substituted cycloalkyl; and D$^-$ is an anion.

2. Compounds of the structure:

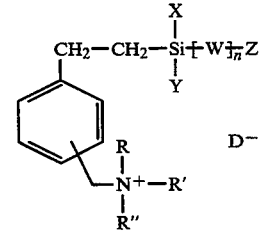

wherein:

X and Y are C$_1$–C$_5$ alkyl, phenyl, or W, wherein W has the structure:

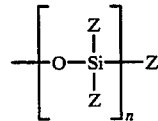

and Z is C$_1$–C$_5$ alkyl and phenyl and n is an integer from zero to five; and R, R', R" are the same or different radicals and are C$_1$–C$_{20}$ alkyl, benzyl, or substituted benzyl, aromatic or substituted aromatic, cycloalkyl, or substituted cycloalkyl; or R, R' and R" are the same or different and are $C_1$–$C_{20}$ aliphatic hydrophilic radicals; and $D^-$ is an anion.

3. A compound with the structure:

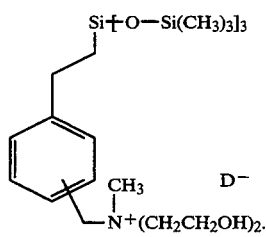

4. Compounds of the structure:

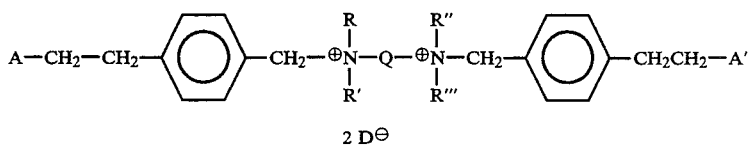

wherein:
A and A' are the same or different and have the structure:

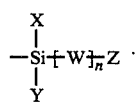

wherein:
X and Y are $C_1$–$C_5$ alkyl, phenyl, or W;
wherein W has the structure:

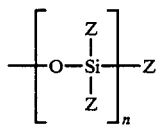

and Z is $C_1$–$C_5$ alkyl or phenyl and n is an integer from zero to five;
R, R', R", R'", are the same or different and are $C_1$–$C_{20}$ alkyl, benzyl, or substituted benzyl, aromatic, or substituted aromatic, or cycloalkyl or substituted cycloalkyl; Q is a radical of linear or branched $C_2$–$C_{20}$ alkyl, unsaturated $C_3$–$C_{20}$ alkyl, $C_2$–$C_{20}$ alkyloxy, aryl or alkyl aryl substituted or unsubstituted, cycloalkyl or substituted cycloalkyl, or a heteroalkyl structure in which the quaternary ammonium atom may or may not be part of the heteroalkyl structure; and $D^-$ is an anion.

5. Compounds of the structure:

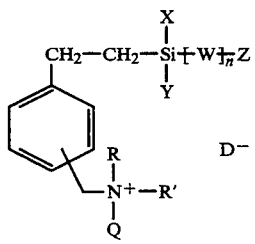

wherein:

X and Y are $C_1$–$C_5$ alkyl, phenyl, or W, wherein W has the structure:

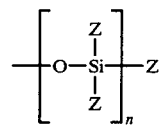

and Z is $C_1$–$C_5$ alkyl or phenyl and n is an integer from zero to five;
R, R' are the same or different and are $C_1$–$C_{20}$ alkyl, benzyl or substituted benzyl, aromatic or substituted aromatic, or cycloalkyl;
Q is alkyl, aryl or cycloalkyl having a polymerizable vinyl group; and
$D^{-1}$ is an anion.

6. Compounds of the structure:

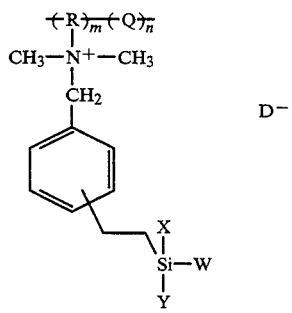

wherein:
R is alkyl, aryl or cyloalkyl having a polymerizable vinyl group;
X and Y are $C_1$–$C_5$ alkyl, phenyl, or W wherein W has the structure:

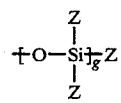

wherein Z is $C_1$–$C_5$ alkyl or phenyl and g is an integer from zero to five;
Q is alklyl, aryl or cycloalkyl having a polymerizable and a water compatible functional group;
$D^-$ is a pharmaceutically acceptable anion; and
m and n are the ratio of the two monomers.

7. The compound of claim 1 selected from the group consisting of:
tris(trimethylsiloxy)silylethyl-m,p-benzyl dimethyl benzyl ammonium chloride, tris(pentamethyldisiloxy)silylethyl-m,p-benzyl trimethyl ammonium chloride, tris(pentamethyldisiloxy)silylethyl-m,p-benzyl dimethyl benzyl ammonium chloride, trimethylsiloxydimethylsilylethyl-m,p-benzyl dimethyl benzyl ammonium chloride, trimethylsiloxydimethylsilylethyl-m,p-benzyl trimethyl ammonium chloride.

8. The compound of claim 2 selected from the group consisting of:

benzenemethanaminium,N,N-dimethyl,N-2-hydroxyethyl-3,4-{2-{bis(trimethyl siloxy)silyl]ethyl}-,chloride;

benzenemethanaminium ,N ,N-dimethyl,N-2-hydroxyethyl-3,4-{2-[tris(trimethyl siloxy)silyl]ethyl}-,chloride;

benzenemethanaminium,N ,N-dimethyl,N-3-hydroxypropyl-3,4-{2-tris(trimethyl siloxy)silyl]ethyl}-, chloride.

9. The compound of claim 4 selected from the group consisting of:

1,6-hexanediaminium,N,N,N',N'-tetramethyl-N ,N'-di-3,4-{2-[tris(trimethyl siloxy)silyl]ethyl}benzyl-,dichloride;

1,4-butanediaminium,N,N,N',N'-tetramethyl-N,N'-di-3,4-[2-(trimethyl siloxy dimethylsilyl)ethyl]benzyl-,dichloride;

1,2-ethanediaminium ,N,N ,N',N'-tetramethyl-N ,N'-di-3,4-{2-[tris(trimethyl siloxy)silyl]ethyl}benzyl-,dichloride;

1,4,-but-2-enediaminium,N,N,N',N'-tetramethyl-N,N'di-3,4-{2-[tris(trimethyl siloxy)silyl]ethyl)benzyl-,dichloride;

1,2-ethanediaminium,N,N,N',N'-tetramethyl-N,N'-di-3,4-[2-(trimethylsiloxy dimethylsilyl)ethyl]benzyl-, dichloride.

10. A compound having the structure:

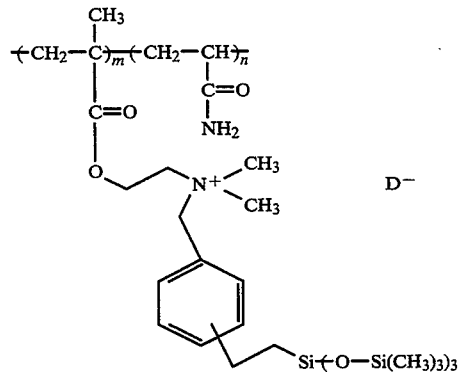

wherein:
m is 1 and n is 1.

11. A compound having the structure:

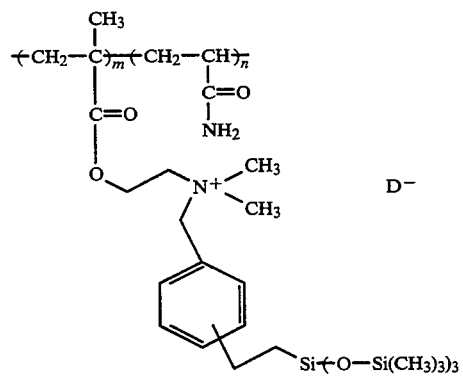

wherein:
m is 1 and n is 0.

* * * * *